United States Patent [19]

Cuppy

[11] Patent Number: 5,755,709
[45] Date of Patent: May 26, 1998

[54] CATHETER SYSTEM FOR PERCUTANEOUSLY INTRODUCING A LIQUID

[76] Inventor: Michael J. Cuppy, 13805 Frontier La., Burnsville, Minn. 55337

[21] Appl. No.: 655,397

[22] Filed: May 30, 1996

Related U.S. Application Data

[63] Continuation-in-part of Ser. No. 637,867, Apr. 24, 1996.

[51] Int. Cl.$^6$ ............................................. A61M 5/178
[52] U.S. Cl. ........................ 604/164; 604/167; 128/754
[58] Field of Search ........................ 128/749, 753, 128/754; 604/160, 161, 164, 165, 167

[56] References Cited

U.S. PATENT DOCUMENTS

| | | | |
|---|---|---|---|
| 3,500,828 | 3/1970 | Podhora | 128/214.4 |
| 3,670,729 | 6/1972 | Bennett et al. | 604/164 X |
| 3,714,945 | 2/1973 | Stanley | 128/214.4 |
| 3,906,930 | 9/1975 | Guerra | 128/2 F |
| 3,977,400 | 8/1976 | Moorehead | 128/214.4 |
| 3,994,293 | 11/1976 | Ferro | 128/214 R |
| 3,995,619 | 12/1976 | Glatzer | 128/754 X |
| 4,106,491 | 8/1978 | Guerra | 128/2 F |
| 4,177,809 | 12/1979 | Moorehead | 128/214.4 |
| 4,200,096 | 4/1980 | Charvin | 128/214.4 |
| 4,230,123 | 10/1980 | Hawkins, Jr. | 128/754 X |
| 4,468,224 | 8/1984 | Enzmann et al. | 604/164 X |
| 4,531,987 | 7/1985 | Yates | 604/164 X |
| 4,549,554 | 10/1985 | Markham et al. | 128/753 |
| 4,578,057 | 3/1986 | Sussman | 604/167 X |
| 4,585,435 | 4/1986 | Vaillancourt | 604/27 |
| 4,588,398 | 5/1986 | Daugherty et al. | 604/265 |
| 4,661,300 | 4/1987 | Daugherty | 264/40.6 |
| 4,664,657 | 5/1987 | Williamitis | 604/265 |
| 4,735,215 | 4/1988 | Goto et al. | 128/754 |
| 4,828,548 | 5/1989 | Walter | 604/164 |
| 4,874,373 | 10/1989 | Luther et al. | 604/164 |
| 4,874,379 | 10/1989 | Gabran | 604/168 |
| 4,893,635 | 1/1990 | DeGroot et al. | 128/754 |
| 4,894,052 | 1/1990 | Crawford | 604/63 |
| 4,907,599 | 3/1990 | Taylor | 128/734 |
| 4,944,308 | 7/1990 | Akerfeldt | 128/754 X |
| 4,994,042 | 2/1991 | Vadher | 604/165 |
| 5,041,087 | 8/1991 | Loo et al. | 604/83 |
| 5,098,410 | 3/1992 | Kerby et al. | 604/256 |
| 5,120,319 | 6/1992 | Van Heugten | 604/168 |
| 5,129,884 | 7/1992 | Dysarz | 604/164 |
| 5,137,515 | 8/1992 | Hogan | 604/110 |
| 5,163,913 | 11/1992 | Rantanen-Lee | 604/177 |
| 5,167,238 | 12/1992 | Newman | 128/760 |
| 5,238,003 | 8/1993 | Baidwan et al. | 128/765 |
| 5,242,411 | 9/1993 | Yamamoto | 604/167 |
| 5,250,038 | 10/1993 | Melker et al. | 604/264 |
| 5,290,246 | 3/1994 | Yamamoto | 604/167 |
| 5,301,686 | 4/1994 | Newman | 128/760 |
| 5,304,136 | 4/1994 | Erskine et al. | 604/110 |
| 5,352,215 | 10/1994 | Thome et al. | 604/284 |
| 5,370,624 | 12/1994 | Edwards et al. | 604/169 |
| 5,400,798 | 3/1995 | Baran | 128/754 |
| 5,417,670 | 5/1995 | Bottlik | 604/264 |
| 5,509,904 | 4/1996 | Kilham | 604/192 |
| 5,542,932 | 8/1996 | Daugherty | 604/168 |
| 5,542,933 | 8/1996 | Marks | 604/188 |

OTHER PUBLICATIONS

Johnson & Johnson Medical Inc., Safety is the Whole Point, Printed in U.S.A. VA394/495 (4 pages). New Preference Owens & Minor, Nursing IV Catheters, pp. 40 and 41.
Becton Dickinson Vascular Access, Insyte AutoGuard Shielded I.V. Catheter, Points to Practice (1 page).

*Primary Examiner*—Sam Rimell
*Attorney, Agent, or Firm*—Larkin, Hoffman, Daly & Lindgren, Ltd.

[57] ABSTRACT

An over-the-needle type IV catheter system comprising a vented "closed hub" catheter assembly having a self-sealing injection port, a check valve operatively associated with the IV line, and a distally-situated flash chamber. Push flanges on the top and sides of the catheter assembly may be used to aid insertion, and may be rotated on the catheter housing as desired. A safety tube assembly having a trigger-actuated spring-biased needle retracting mechanism and a telescoping safety guard permit the operator to enclose the needle after catheterization using one hand. The coupling for the IV line is oriented in generally the same direction as the catheter tube, so that looping the IV line is unnecessary.

39 Claims, 11 Drawing Sheets

CATHETER SYSTEM FOR PERCUTANEOUSLY INTRODUCING A LIQUID

CROSS REFERENCES TO CO-PENDING APPLICATIONS

This is a continuation-in-part (CIP) of Pat. application Ser. No. 08/637,867 of the same title filed on Apr. 24, 1996, and the benefit of priority under 35 USC §120 is hereby claimed from that application.

BACKGROUND OF THE INVENTION

1. Field of the Invention

The present invention relates to intravenous (IV) catheterization, and more particularly to a catheter system comprising a vented distal flash chamber, distally-oriented IV line connection, separate self-sealing injection port, and detachable needle guard having a spring-biased trigger-actuated needle retraction mechanism

2. Description of the Prior Art

The field of IV catheters and over-the-needle catheterization devices is relatively well know. The most frequently used catheters include a molded hub and flexible sleeve, through which a steel catheterization needle is placed. The needle and sleeve are inserted through the patient's skin and advanced into a vein or artery, the needle is withdrawn rearwardly through the catheter hub, and an IV or syringe is then attached to the catheter hub.

These systems are generally characterized as "open hub" configurations because no structure blocks the flow of blood from the patient through the sleeve and catheter hub as the needle is withdrawn from the catheter hub, and the rear of the catheter hub is exposed to the environment both during insertion and advancement of the catheter, and subsequent to insertion when IV lines or medication syringes are being replaced or switched.

Both in the field and in hospital or health care facilities, the open hub configuration presents many problems.

First, there are risks to the patient because a sterile field is not maintained at the rear of the catheter hub, and the operator must frequently touch and push against the back of the catheter hub to advance the catheter. The operator may also place a finger over the open hub once catheterization is complete, to stop the outward flow of blood until an IV line or syringe can be attached to the hub. The same procedure may be used when switching IV lines or syringes, which compounds the opportunities to introduce infectious agents into the patient's bloodstream or contaminate the IV or syringe equipment. Since an operator may need to work rapidly on several patients in a trauma situation without changing gloves, this increases the opportunity to transmit viral or infectious agents back and forth between patients.

Second, there is a risk to the health care professional, since the operator is necessarily exposed to blood during catheterization, when switching IV lines or medication syringes, and to the expelled blood which remains on the patient, the patient's or operator's clothing, or objects in the surrounding scene where care is being provided. While health care providers may frequently be exposed to blood when treating a trauma or during surgery, exposure to blood when initiating or changing an IV line or medicating a patient in a controlled health care environment presents a separate and wholly unwarranted risk. Although the risk of contracting an infectious or transmissible disease from exposed blood may be statistically low (compared to needle sticks, for example), the complete prevention of unnecessary risks and concern for the psychological well-being of the health care provider are certainly valid considerations.

Third, although a trauma scene may be graphic and bloody, additional expulsion of blood during catheterization or medication may present further problems. A patient may lose their composure or react precipitously if they see their (or another person's) blood being expelled or jetted from catheter hub. This can undue the work that a trauma specialist has put into quieting a patient. The expelled blood may require the health care professional to lose time wiping off their hands and equipment before continuing to provide care, and the need to deal with expelled or jetted blood (even when expected) can be distracting or annoying when the operator is trying to focus their attention on diagnosis and treatment. When unexpected (such as if an IV line or syringe is pulled free when unattended), the results can be startling and inopportune, requiring the health care provider to stop giving treatment to the patient (or another person) in order to halt the uncontrolled blood flow, recatheterize, start an IV or medication, clean up, and then return to treatment.

Virtually all current IV catheters can have a "heparin lock" attachment added to the catheter hub after an IV is started, which if not done quickly and correctly will result in a serious risk of blood exposure.

The current method of drug administration is to inject the drug up to eight inches further up the IV line, where the first medication port is usually located. This can adversely affect the effectiveness of time- or concentration-sensitive drugs. Emergency medications like adenosine (extremely time sensitive) can be ineffective when injected further from the site of the IV. It may also be necessary to manually squeeze the IV bag to ensure that an entire metered dose of medication is transferred rapidly from the IV line into the patient.

Existing catheter systems particularly those having retractable needles and guards) locate the "flash chamber" too far back on the needle (where the operator's hand screens the normal line of sight), resulting in delayed or concealed visualization of the flash when successful catheterization has been achieved. Each time the operator repositions their hand to confirm whether a flash is visible, the manipulation risks causing the needle tip to be dislodged from the vein and precipitating an unsuccessful IV attempt, or may cause the operator to lose their initial alignment with a selected vein or artery.

Many current style IV catheters do not provide any automatic protection from needle punctures or "sticks." The operator has to manually "re-cap" the needle (presenting the greatest risk of a needle stick), or set the needle aside until the IV is started and then remember to count and safely dispose of all needles that were used. Other "safety needles" requires the operator to manually retract the needle all the way back until it locks into a protective guard, but it frequently happens that people forget to fully retract the needle into the locked position, allowing the needle to slip out of safety tube and again risking a needle stick or puncture of a the disposal receptacle. Some safety needle designs adequately protect the user from needle punctures, but have residual blood dispersed over the end of the safety guard where the hub seal or blood stopper is located.

The newer "safety IV catheters" do not allow access to draw a blood sample after insertion, such as for blood sugar analysis. In order to collect blood for analysis, the operator must draw a separate blood sample using a vacuum hemotube or lancet, again exposing the patient and operator to the same risks of blood exposure, infection, and spillage.

Currently-marketed IV catheters hubs do not provide an adequately designed structure for inserting and advancing the IV needle into a vein after the initial blood flash-back. Most are either nonexistent or too small or smooth to be effective, thereby reducing the chance of successful catheter insertion. Consequently, most operators must push directly on the exposed back opening of the catheter hub with their finger or thumb, as described above.

Existing "open hub" catheters do not provide any protection from blood regurgitation up the IV line when the IV bag is set down or dropped. This usually results in blood clotting within the catheter hub or IV line, forcing the operator to discontinue using that IV line and necessitating another catheterization and IV start. IV lines will also frequently need to be replaced for other reasons, and when the old line is disconnected it will leak or jet blood until a new line is attached. If this is not done quickly and correctly, there is a serious risk of blood exposure. No marketed open-hub IV currently provides a safe and blood-free method to change or swap IV lines.

Similarly, open hub IV catheters do not provide any protection from blood exposure if the IV line is accidentally or purposefully disconnected from IV catheter, such as if the line is caught on an object during transportation, the patient moves or intentionally pulls the IV line out, or in the occasional event of a catheter expulsion due to natural blood pressure (for example, when arterial catheterization is mandated). If this occurs, a serious blood contamination problem will exist until the IV line can be either reconnected or discontinued, which may take some time even if detected immediately, and in some cases the additional blood loss can adversely affect the patient's condition.

The current state of available IV catheters is therefore woefully inadequate, and in fact unnecessarily dangerous to both the patient and health care provider.

SUMMARY OF THE INVENTION

The general purpose of the present invention is a "bloodless" or "closed-hub" catheter system that provides both a check valve built into the IV port and a self-sealing injection site which serves as a second port for sampling, heparin locking, or the administration of medication. This catheter system allows the operator to start an sterile IV in a manner which minimizes or negates any exposure to expelled blood and needle punctures.

This catheter system has several functions and advantages. The check valve permits the flash chamber to vent, but prevents the egress of blood during catheterization and at all times subsequent to catheterization. The check valve therefore prevents blood from entering the IV line if the IV bag is lowered, if a heparin or saline flush is performed, or during blood sampling. The check valve prevents the patient from bleeding in the event the IV line is accidentally severed or the IV tube is separated from the catheter hub. The vent cap initially provides a sterile field for connecting an IV, and the check valve permits IV substitutions without blood leakage, and while maintaining suitably sterile conditions. Recatheterization of trauma patients at a hospital or care facility can be avoided.

The location of the flash chamber at the forward end of the hub permits rapid visualization of flashing immediately upon entry into a vein or artery, and the use of a spring-biased trigger-actuated needle retraction mechanism permits the use of a side aperture on the needle within the forward flash chamber without blood leakage, exposure, or loss of sterility. It also permits direct visualization of injected medications within a bolus at a point closest to entry into the patient, as with a conventional syringe injection.

The vent cap and IV connector point towards the patient, so that looping and taping the IV tube is unnecessary. This reduces the risk that an IV line will get caught or snagged during transportation or treatment, or that the tube will become kinked. It also frees up several additional inches of IV tubing to make handling the IV bag easier, and there is no loop to exert additional pressure on the adhesive tape which might cause it to pull free. The IV line is then directed away from the self-sealing injection port, so that medication can be administered without interference or tangling the IV line. The shape of the catheter housing provides a better attachment to the patient's arm or hand when taped, with less change for the catheter to pull free of the tape.

The self-sealing injection port permits the patient to be medicated or blood samples to be drawn without disconnecting the IV line or initiating a second catheterization. The check valve operates automatically when fluid pressure inside the closed hub increases, thereby permitting options such as the injection of medication, performing flushes or heparin locking, or withdrawal of blood samples under pressure without medication, fluid, or blood backing up the IV line. Since the check valve operates automatically, the IV line is restored to full operation immediately upon the medication being administered or the flush being performed. The self-sealing injection port may also serve as the site for a second or further "piggy-backed" IV line without a second catheterization, and still permits the injection of medications or blood sampling.

The shape of the catheter housing itself provides a better grip for inserting and advancing the catheter, and direct tactile feedback of the "pop" detected when successful catheterization is achieved. The rotatable forward push flange permits enlarged pressure areas on the opposing sides of the catheter assembly, and the flange may be rotated so that the enlarged areas do not interfere with taping the catheter to the patient's arm or hand. Additional stationary push flanges located in accessible areas such as the top of the housing allow more positive control over positioning or advancing the catheter assembly, and may be designed to increase the operator's ability to grip the flanges with a fingernail or fingertip.

Use of the spring-biased trigger-actuated needle retracting mechanism during the actual catheterization ensures that the needle is retracted before the catheter assembly is removed from the safety tube assembly, thereby mitigating against operators forgetting to retract the needle, failing to retract the needle fully, or accidentally sticking themselves prior to or while retracting the needle. The telescoping tube permits the overall length of the catheter system to be substantially the same as or even shorter than existing open-hub catheters having needle retracting mechanisms, yet have the additional features described herein.

Briefly described, the invention comprises an over-the-needle type IV catheter system having a vented "closed hub" catheter assembly with a self-sealing injection port, a check valve operatively associated with the IV line, and a distally-situated flash chamber. Push flanges on the top and sides of the catheter assembly may be used to aid insertion, and may be rotated on the catheter housing as desired. A safety tube assembly having a trigger-actuated spring-biased needle retracting mechanism and a telescoping safety guard permit the operator to enclose the needle after catheterization using one hand. The coupling for the IV line is oriented in generally the same direction as the catheter tube, so that looping the IV line is unnecessary and the IV line is directed away from the self-sealing injection port.

DETAILED DESCRIPTION OF THE PREFERRED EMBODIMENTS

The catheter system of this invention is shown in FIGS. 1–16 and referenced generally therein by the numeral 10. For clarity and convenience, both the inventive apparatus and its method of use are referred to interchangeably herein as the catheter system 10.

Figure 1:
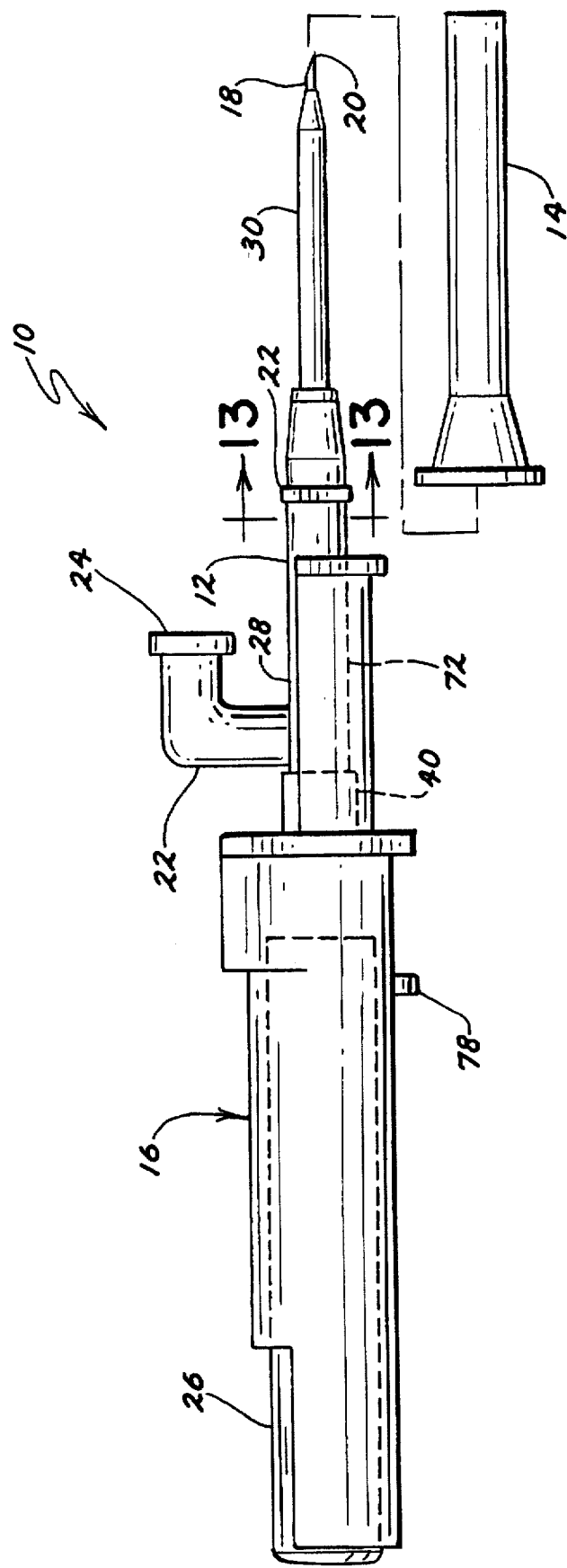
FIG. 1 is a partially exploded side elevation view of the catheter system of the present invention with various components shown in phantom.

Referring particularly to FIG. 1, a first representative embodiment of the catheter system 10 is shown composed of an over-the-needle type catheter assembly 12 initially enclosed by a protective cap 14 and disposed at the front or distal end of the catheter system 10, and a safety tube assembly 16 disposed at the rear or proximal end of the catheter system 10. The catheter assembly 12 includes a relatively long venous-gauge coring-tipped needle 18 having an angled distal point 20 for percutaneous penetration of a patient's skin and vascular system, a plurality of push flanges 22 for advancing the needle 18 and catheter assembly 12, and a vent cap assembly 24. The safety tube assembly 16 includes a spring-biased telescoping tube 26.

Figure 2:
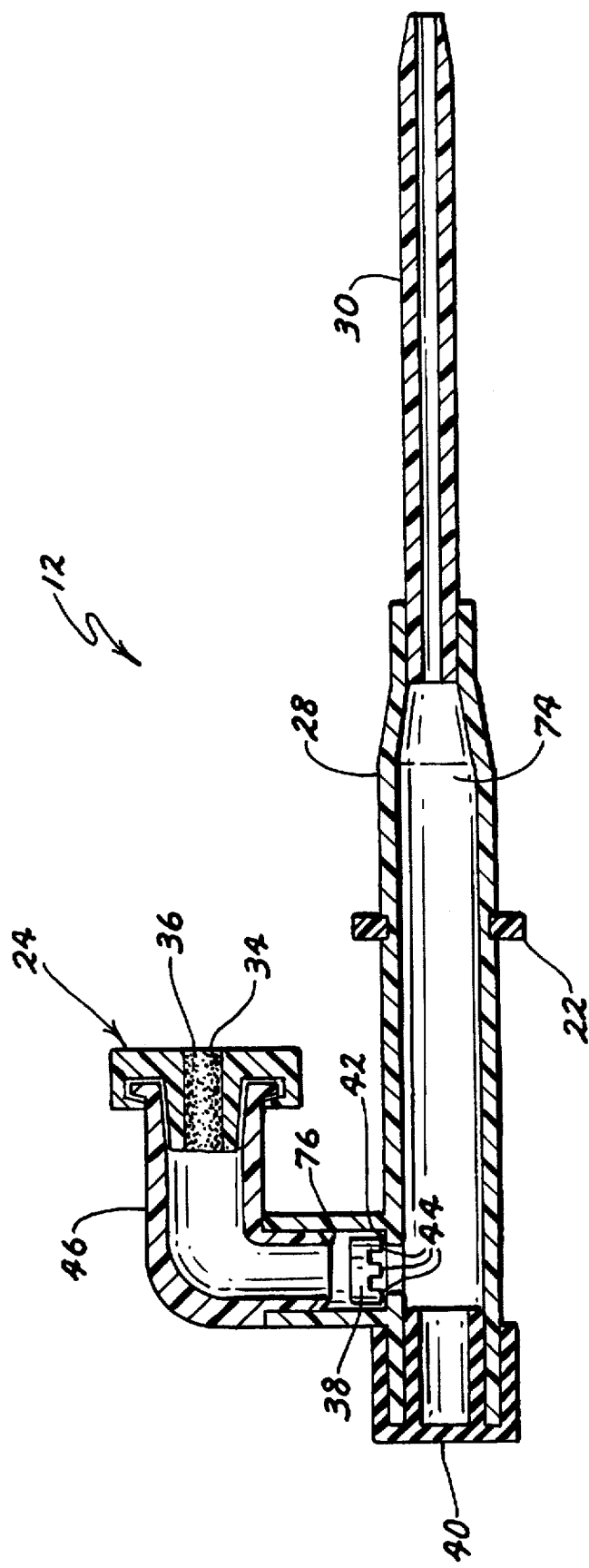
FIG. 2 is a side cross section view of the catheter and closed hub of the catheter system of FIG. 1.

Referring to FIGS. 1 and 2, the catheter assembly 12 is shown as having a "closed hub" configuration as described further herein. Housing 28 has a generally U-shaped configuration including a generally cylindrical body section and a vent cap region, the vent cap region extending from and forming a 90° elbow relative to the body section, and oriented in a generally distal direction corresponding to the direction of extent of the body section. The body section of the housing 28 supports a generally flexible over-the-needle type catheter tube 30 or sleeve extending distally from and partially received within the generally cylindrical open distal neck of the housing 28. The vent cap section of the housing 28 similarly includes a generally cylindrical wall defining a distal opening into which a vent cap 24 is engagingly received, the vent cap 24 defining an aperture 34 filled with a porous gas-transmitting material 36 such as cotton for venting air or other trapped gases from within the interior region of the housing 28. A check valve 38 is slidably disposed within the vent cap portion of the housing 28 for linear movement toward and away from the main interior region of the body section of the housing 28 (and therefore the vent cap 24). The rear or proximal portion of the housing 28 at or behind the juncture of the body section and the vent cap section defines a generally cylindrical opening which is sealingly covered by a self-sealing injection port 40, which envelopes and is engagingly received within the wall of the housing 28. The check valve 38 seats in its most proximal position against an inwardly extending radial flange 42 by contact with a plurality of depending feet 44 extending from the body of the check valve 38 and defining a plurality of openings therebetween to permit the passage of gases. The distal end of the vent cap 24 forms a coupling region 46 designed to mate with a conventional coupling used in medical applications, such as a lure lock. The vent cap assembly 24 also forms a removable protective vent cap 24 to maintain the sterility of the interior of the catheter system 10 and the sterile field surrounding the vent cap assembly 24 and portion of the coupling 46 to which an IV line is connected.

Figure 3:
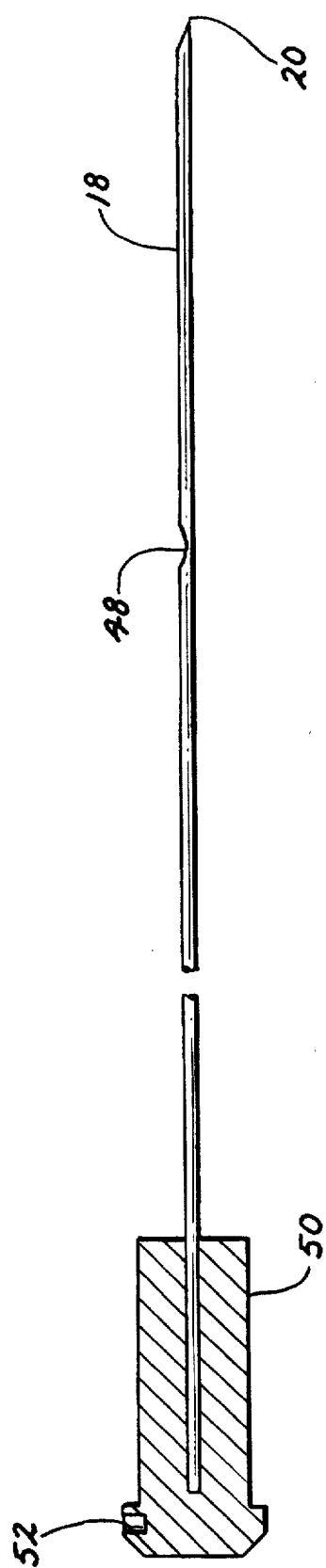
FIG. 3 is a partially broken away side cross section view of the needle and needle carrier of the catheter system of FIG. 1.
Figure 4:
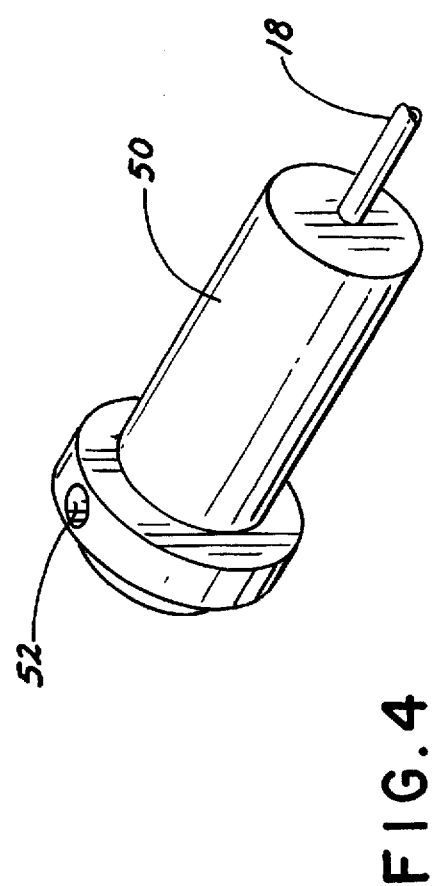
FIG. 4 is a perspective view of the needle carrier of FIG. 3.

Referring to FIGS. 3 and 4, the needle 18 is shown defining a side aperture 48 positioned along the needle 18 at a point sufficiently proximal to the rear end of the catheter tube 30 such that the side aperture 48 will dispense blood into the interior region of the body section of the housing 28, in a manner so as to be visible through a transparent distal region of the housing 28. The side aperture 48 is shown for illustrative purposes as an elongated opening or groove, but it may be appreciated that a small bore hole oriented perpendicular to or at an angle relative to the longitudinal axis of the needle 18 may be sufficient in most applications. The proximal end of needle 18 is shown fixedly attached to and partially embedded in a needle carrier 50 or shuttle which is sized and geometrically configured so as to be engaged and slidably received within the safety tube assembly 16 as described in further detail below, and to maintain a proper orientation of the needle 18 within the housing 28 and catheter tube 30. In the embodiment shown, the needle carrier has an outwardly-extending radial flange having a beveled rear surface disposed at the proximal end thereof. The needle carrier 50 further defines a trigger pin receiving aperture 52 extending radially inward into the radial flange generally perpendicular to the common longitudinal axis of the needle carrier 50 and needle 18, and therefore disposed generally adjacent to the proximal end of the needle carrier 50 for use in restraining and releasing the needle carrier 50 as later described herein.

Figure 5:
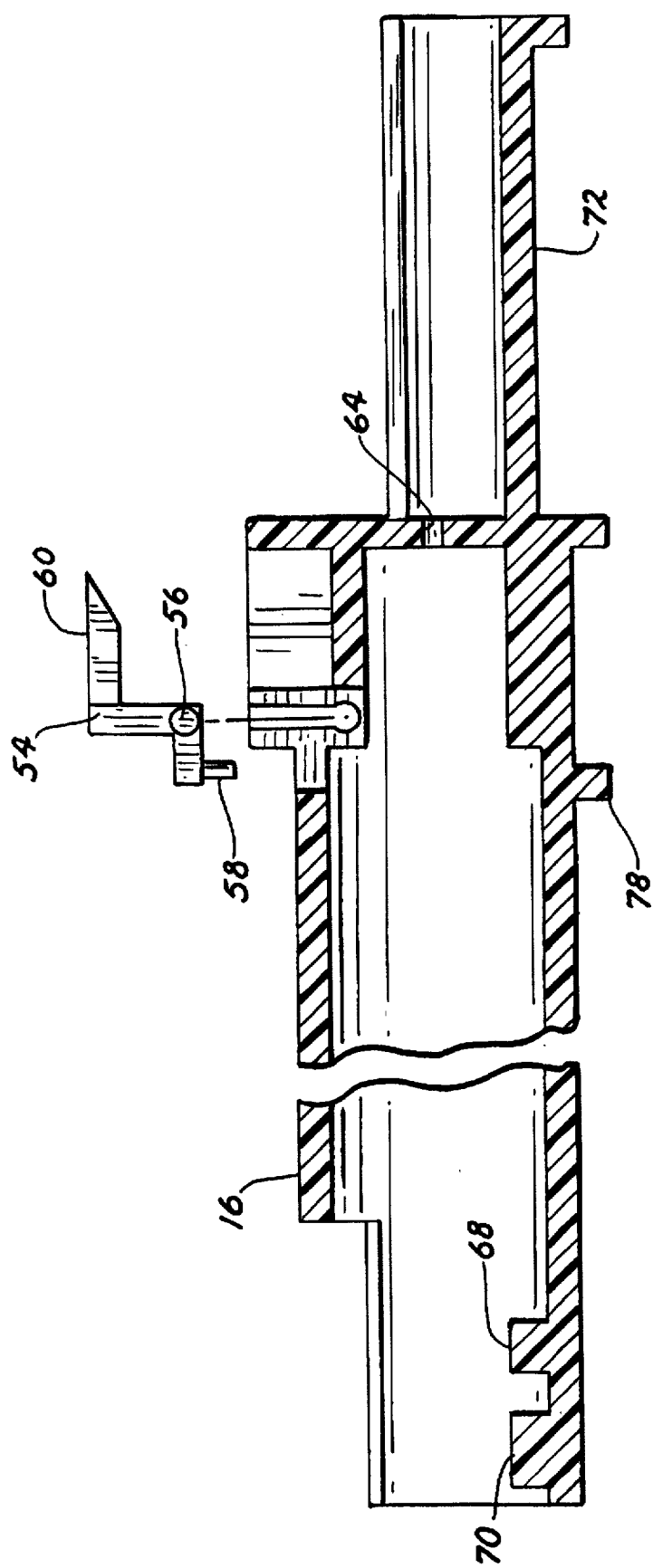
FIG. 5 is a partially exploded side cross section view of the safety tube assembly and trigger of the catheter system of FIG. 1.
Figure 6:
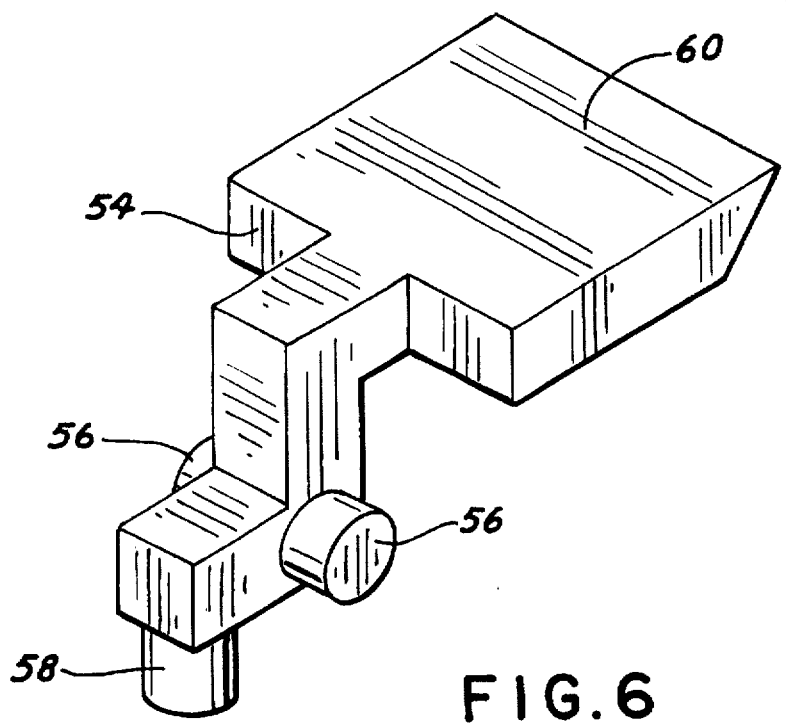
FIG. 6 is a perspective view of the trigger of FIG. 5.
Figure 7:
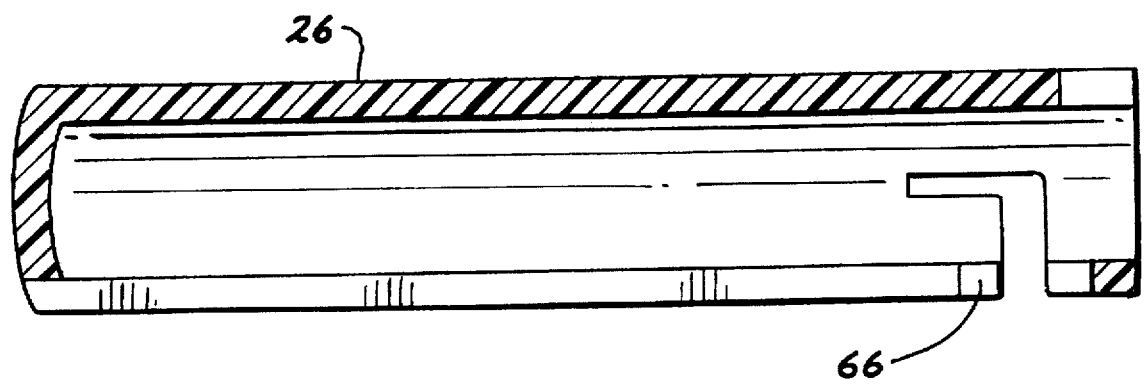
FIG. 7 is a side cross section view of the telescoping tube portion of the safety tube assembly of the catheter system of FIG. 1.

Referring particularly to FIGS. 5–8, the components of the safety tube assembly 16 are shown in greater detail. In FIG. 5, a generally Z-shaped trigger member 54 is shown in an unassembled or unmounted position disposed closely above a pair of generally vertical grooves defined by the housing wall of the safety tube assembly 16. The trigger member 54 is forcibly inserted and slidingly received within the grooves until each generally cylindrical pivot axis 56 is engaged within a corresponding semicircular channel at the base of each corresponding groove, such that the trigger member 54 is maintained in proper orientation and rocks or pivots freely about the opposed pivot axes 56 relative to the housing wall of the safety tube assembly 16. Trigger pin 58 depends from the bottom surface of the proximal-extending lower leg of the trigger member 54, and is positioned so as to be at least partially received within and engage the trigger pin receiving aperture 52 defined in the top side of the needle carrier 50. To disengage the trigger pin 58 from the trigger pin receiving aperture 52, the top actuation surface 60 of the forwardly-extending distal leg of the trigger member 54 is depressed by the operator applying fingertip pressure downwardly (or radially inward) against the actuation surface 60, thereby causing the trigger member 54 to pivot about the pivot axes 56 and lift the trigger pin 58 as later described in detail, for actuation of the spring biased needle 18 and its components into the spring biased telescoping needle tube 26.

The trigger pin 58 may be press fit into the trigger pin receiving aperture 52 to provide initial resistance when actuating the trigger member 54, this threshold pressure preventing the premature or accidental release of the trigger pin 58 from the trigger pin receiving aperture 52. Alternately, the channels and the pivot axes 56 may be shaped in a manner so as to having mating surfaces requiring that a predetermined initial pressure be applied to rotate the trigger member 54 about the pivot axes 56 from the engaged towards the released positions, the trigger pin 58 and trigger pin receiving aperture 52 may define surfaces or detents that retain the trigger pin 58 within the trigger pin receiving aperture 52 until the predetermined threshold pressure is applied, or the distally-extending upper leg of the trigger member 54 may be biased upwardly (or radially outward) using a compression spring or a pivoting spring member formed in the housing of the safety tube assembly 16.

Figure 8:
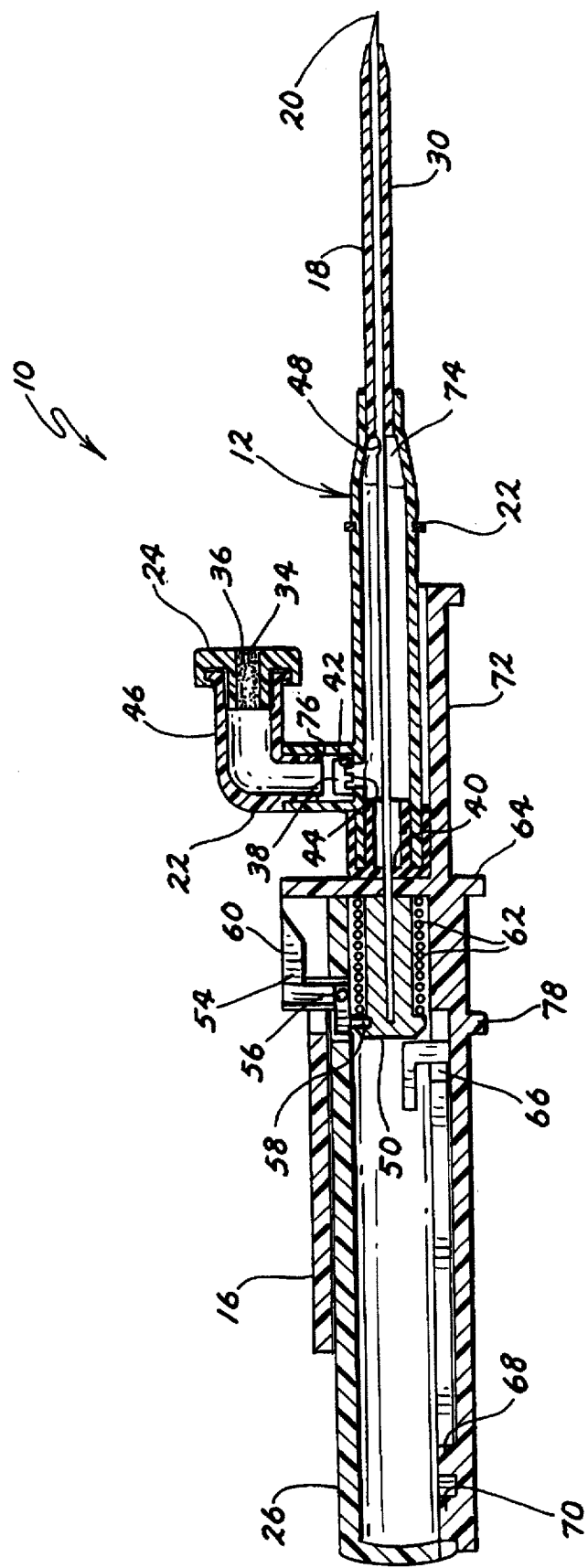
FIG. 8 is a side cross sectional view of the catheter system of FIG. 1.
Figure 9:
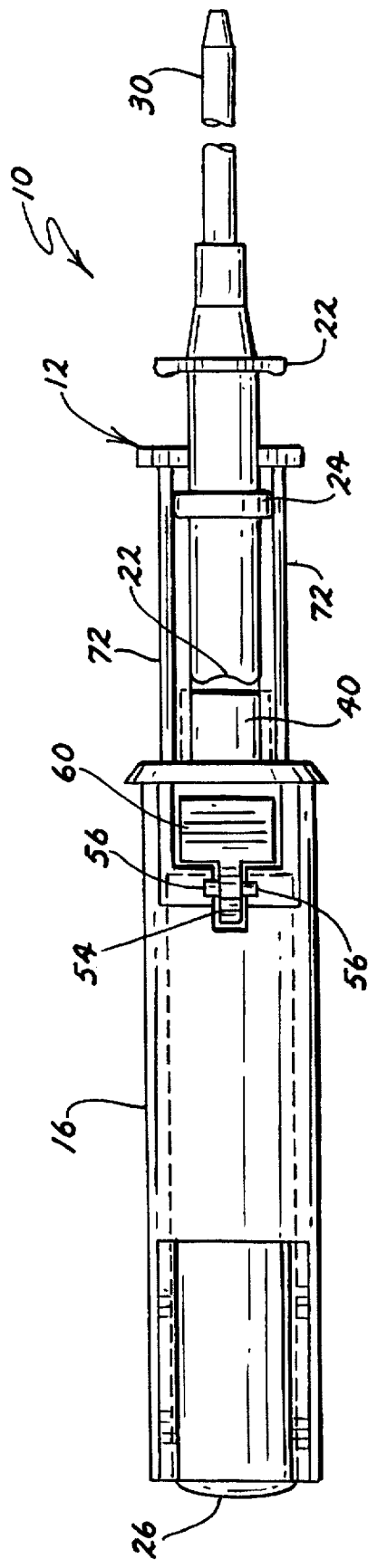
FIG. 9 is a top view of the catheter system of FIG. 1.
Figure 10:
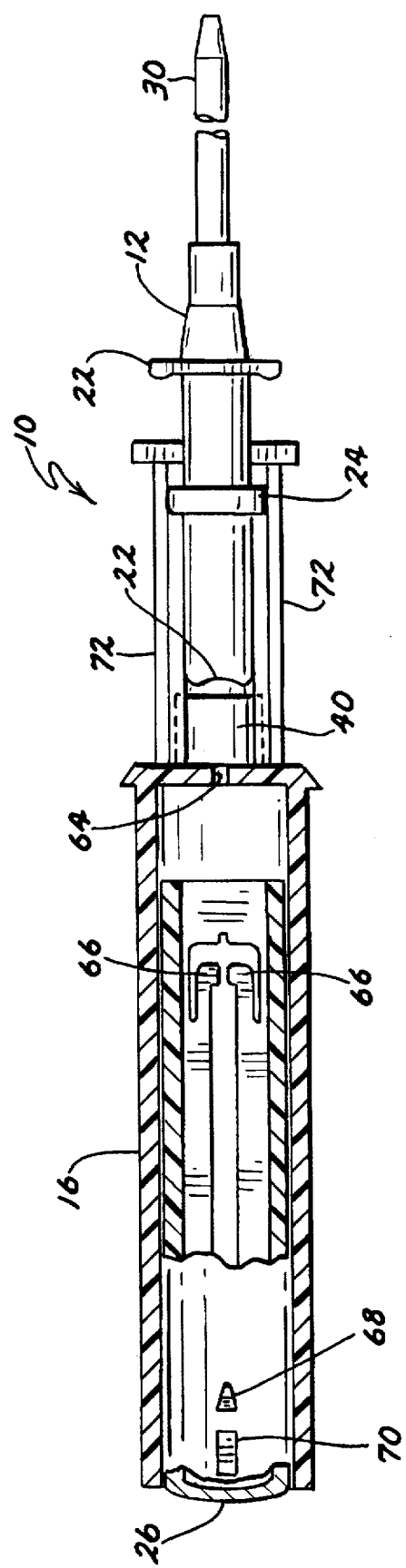
FIG. 10 is a partially broken away top cross section view of the catheter system of FIG. 9.
Figure 11:
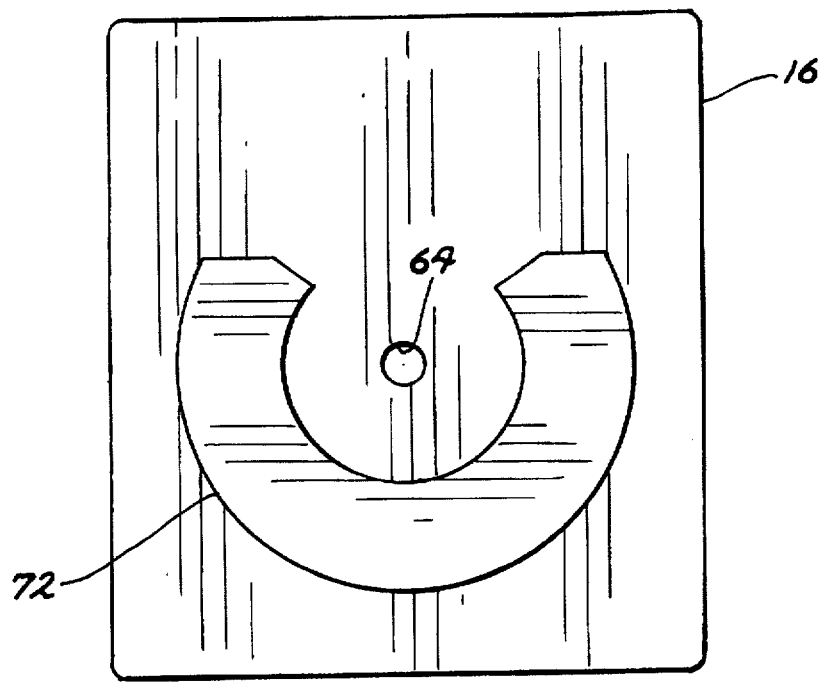
FIG. 11 is a front view of the safety tube assembly of the catheter system of FIG. 1 taken from the right with the catheter assembly removed.
Figure 12:
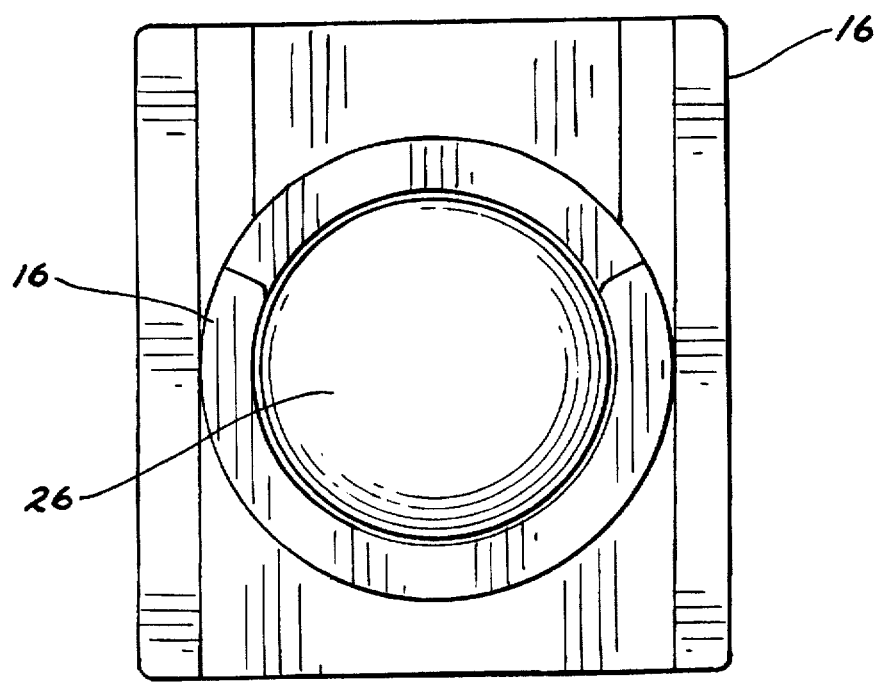
FIG. 12 is a rear view of the catheter system taken from the left in FIG. 1.
Figure 13:
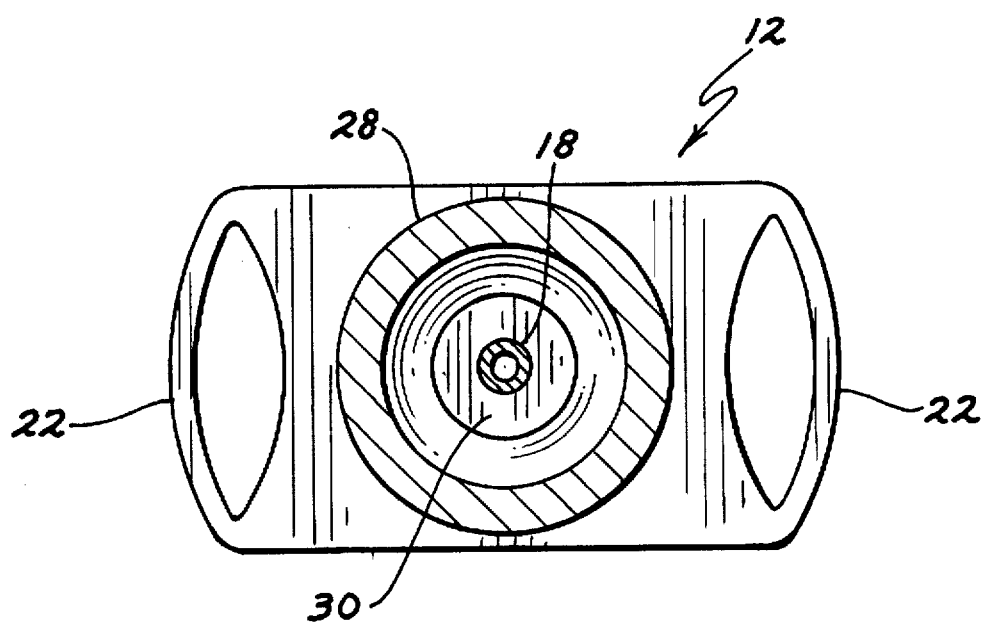
FIG. 13 is a rear cross section view of the catheter assembly showing the forward push flange.
Figures 14, 15:
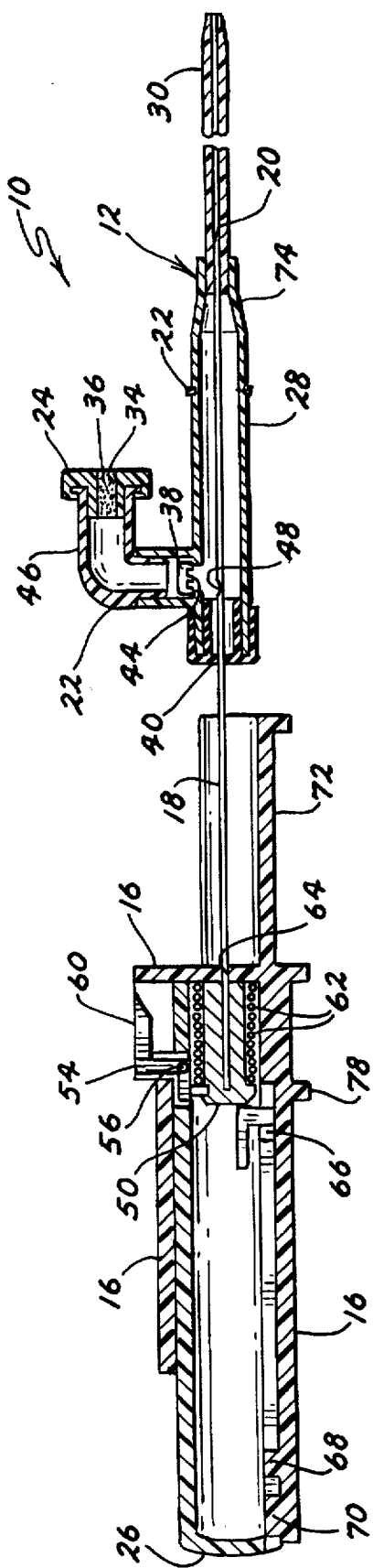
FIG. 14 is a side cross section view of the catheter system of FIG. 1 with the catheter assembly disengaged from the safety tube assembly.
FIG. 15 is a side cross section view of the catheter system of FIG. 1 showing the catheter assembly separated from the safety tube assembly, with the telescoping tube and needle in the retracted position for disposal.

Referring to FIGS. 8, 10, and 14, it may be appreciated that if the trigger member 54 is actuated so as to disengage the trigger pin 58 from the trigger pin receiving aperture 52, the rearward force exerted on the needle carrier 50 by the coil-type compression spring 62 disposed within the distal end of the housing of the safety tube assembly 16 and circumscribing the generally cylindrical distal segment of the needle carrier 50 will cause the needle carrier 50 to be rapidly propelled axially toward the proximal end of the safety tube assembly 16, and thereby simultaneously cause the distal point 20 of the needle 18 to be withdrawn from the patient and retracted through the catheter tube 30 and self-sealing injection port 40 at the proximal end of the closed hub catheter assembly 12.

It may therefore be readily appreciated that the needle 18 will normally be withdrawn from the patient into the fully retracted position within the safety tube assembly 16 almost instantaneously (and much faster than could safely be accomplished manually), so that blood will not leak or be expelled from the side aperture 48 of the needle 18. It is anticipated that embodiments may be adapted which will close the side aperture 48 during retraction of the needle 18, for example by placing a radially extending flange (not shown) on the needle 18 just distal to the side aperture 48 which strips a thin tubular sleeve (not shown) onto the needle 18 in covering relation to the side aperture 48 as the needle 18 and flange pass through the self-sealing injection port 40.

As the needle carrier 50 and needle 18 are moved rearwardly by the compression spring 62, the rear face of the needle carrier 50 will contact the confronting inner surface of the telescoping tube 26 (which is slidingly mounted within the forward housing segment of the safety tube assembly 16) once the needle 18 is withdrawn or retracted approximately half its length, and the needle carrier 50 and compression spring 62 will exert rearward pressure on the telescoping tube 26 causing the telescoping tube 26 to slide proximally relative to the forward housing segment of the safety tube assembly 16 until the telescoping tube 26 is disposed in its fully extended position, at which point the needle 18 will have been withdrawn completely through the aperture 64 in the front face of the safety tube assembly 16, and the needle carrier 50 and needle 18 will be in their fully retracted position with the entire needle 18 including the distal point 20 disposed within and protected from physical contact by the safety tube assembly 16.

Referring particularly to FIGS. 10, 14, and 15, the telescoping tube 26 defines a longitudinal opening which terminates at its distal end in a T-shaped segment which forms a pair of inwardly-projecting and closely confronting locking arms 66 disposed in the wall of the telescoping tube 26. When viewed from the side as in FIG. 14, this opening defines a generally L-shaped aperture due to the curvature of the wall of the telescoping tube 26, with the locking arms 66 disposed along the bottom surface of the telescoping tube 26. As the telescoping tube 26 moves rearwardly to its extended position, the beveled or ramped wedge segment 68 projecting upwardly from the bottom of the housing of the safety tube assembly 16 traverses along the longitudinal opening, and passes between the locking arms 66, causing those arms to spring open slightly. As the wedge segment 68 passes forwardly beyond the locking arms 66, the locking arms 66 snap inwardly toward one another and lock between the wedge segment 68 and the stop or locking member 70, which also prevents further rearward movement of the telescoping tube 26.

With the inwardly-projecting portions of the locking arms 66 engaged between the wedge segment 68 and the locking member 70, the telescoping tube 26 is prevented from being accidentally or inadvertently compressed axially, or otherwise overcoming the pressure exerted by the compression spring 62 to expose the distal point 20 of the needle 18 through the aperture 64. Since the distal point 20 of the needle 18 is not supported once it passes rearwardly through the aperture 64, the distal point 20 of the needle 18 will usually shift or tip to the side of the safety tube assembly 16 and out of alignment with the aperture 64, thereby also preventing the needle 18 from exiting the safety tube assembly 16.

The catheter assembly 12 may be connected or secured to the safety tube assembly 16 by frictional engagement between the outer surface of the needle 18 and the polymeric self-sealing injection port 40, or the housing 28 of the catheter assembly 12 may include a locking mechanism that engages a mating section of the housing on the safety tube assembly 16, and which may be easily disengaged by the operator by twisting or axial pulling the catheter assembly 12 and safety tube assembly 16 apart from one another.

The housing 28 of the catheter assembly 12 and the housing of the safety tube assembly 16 and safety tube 26 may be molded or otherwise fabricated from a plastic resin, and include a grip area 72 which (together with the push flanges 22) may be textured or surfaced as desired to provide a positive forward friction for insertion of the needle 18 and catheter tube 30 through the skin and into the vascular system of the patient. The grip area 72, shown particularly in FIGS. 8, 9, and 11, forms a U-shaped channel partially enclosing the bottom side of the proximal end of the catheter assembly 12. The surface of the safety tube assembly 16 may similarly be textured or surfaced to provide positive rearward friction for withdrawing the needle 18 through the self-sealing injection port 40. The push flanges 22 are disposed and oriented so as to provide a purchase for a finger or fingernail of the operator. The housing 28 of the catheter assembly 12 and the housing of the safety tube assembly 16 and safety tube 26 may be any color or opacity, however at least the distal portion of the housing 28 of the catheter assembly 12 should define a generally clear translucent region to serve as a visual indicator or window surrounding or visually exposing the flash chamber area 74 of the interior of the body section of the catheter assembly 12.

Figure 16:
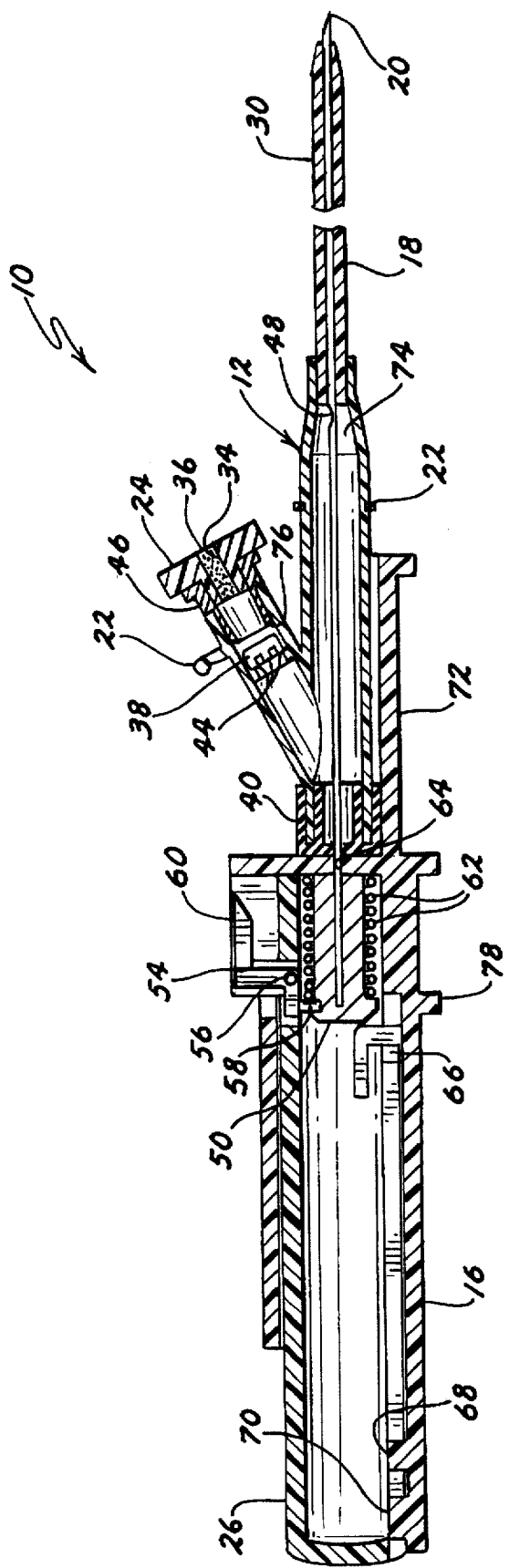
FIG. 16 is a side cross section view of an alternate embodiment of the closed hub and catheter of this invention.

Referring particularly to FIG. 16, an alternate embodiment of the catheter system 10 is shown in which the vent cap section of the housing 28 of the catheter assembly 12 defines a generally angled segment extending radially outward at an acute angle relative to the longitudinal axis of the body section of the housing 28, and similarly extending forwardly or distally in generally the same direction as the body section of the housing of the catheter assembly 12. An angle of between 30° and 60° has proven suitable, however the angle may be selected as desired based upon any appropriate criteria.

The forward push flange 22 if fabricated from a unitary member which is snap fit onto the exterior of the housing 28 and rotates within a radial groove circumscribing the housing 28 of the catheter assembly 12. The forward push flange 22 is thereby maintained in a predetermined axial location and generally perpendicular to the housing 28, thus permitting the enlarged sections of the forward push flange 22 to be rotated to a desired orientation relative to the vent cap section of the housing 28 for insertion of the needle 18 and catheter tube 30, or to be rotated to a non-interfering position when the catheter assembly 12 is taped to the arm or hand of the patient. While a generally oblong or rounded-rectangular shape has proven suitable for the forward push flange 22, it may be fabricated having any uniform or non-uniform shape that is desired, permitting the operator to select the desired size, shape, and orientation of the push flange 22 or its enlarged sections that are optimal for a given situation. Regions of the forward push flange 22 may also include an arc-shaped groove to match the tip of an operator's fingernail as shown with respect to the rear or upper stationary push flange 22, to thereby provide a more secure pushing surface.

In operation, the catheter system 10 is initially provided to the operator in a completely assembled condition, contained in a sterile, sealed package. The operator completely or partially removes the catheter system 10 from the packaging, and removes the protective cap 14 to expose the catheter tube 30 and distal point 20 of the needle 18.

The operator grips the catheter assembly 12 applies forward pressure against the gripping area 72 or exposed upper portion of the U-shaped housing 28 to pierce the skin of the patient in the area in which catheterization is desired using the distal point 20 of the needle 18, and then continues to insert the needle 18 and catheter tube 30 until successful entry into a vein or artery (as desired) is achieved. It has proven beneficial for the operator to grip or at least rest a finger on the gripping area 72 and exposed upper portion of the U-shaped housing 28, since this transmits the "pop" or sharp vibration that can be felt as the distal point 20 of the needle 18 fully penetrates the wall of the vein or artery and enters the vessel. As the distal point 20 of the needle pierces that corresponding vessel, blood will flow under the available systolic or diastolic pressure through the needle 18 and exit through the side aperture 48 and be visible in the flash chamber area 74 of the interior region of the catheter assembly through the transparent window of the housing 28 closely adjacent to the forward section of the housing 28 and not obstructed by the operator's fingers. It may be appreciated that in most intravenous (IV) catheterizations, the needle 18 and catheter tube 30 will be inserted into a vein in the patient's arm or hand and oriented such that distal end is facing upward toward the shoulder and torso of the patient and the needle 18 and catheter tube 30 are generally parallel with the longitudinal axis of the patient's arm. The vent cap assembly 24 will be similarly oriented upward along the arm and toward the shoulder and torso of the patient.

Air or other gases within the interior region of the housing 28 are displaced by blood flowing into the catheter assembly 12, and vented through the check valve 38 and aperture 34 in the vent cap assembly 24. Blood will fill the interior region of the catheter assembly 12, deflect off the self-sealing injection site 40, and flow into the lower portion of the vent cap section of the housing 28 below the check valve 38. As blood contacts the base of the check valve 38, hydraulic pressure will push the check valve 38 upwardly against the opposite valve seat 76 to close off the valve opening and seal off any blood flow through the vent cap assembly 24. The check valve 38 in conjunction with the self-sealing injection port 40 thereby effectively seal the flash chamber 74 and interior of the catheter assembly 12 to form the "closed hub" configuration, while still allowing air to be initially vented from the catheter assembly 12.

The operator will then hold inserted catheter assembly 12 with one hand and hold the safety tube assembly 16 with the other hand, with projection 78 on the bottom of the safety tube assembly 16 orienting the operator's index finger and hand so that the palm or fingers do not block the telescoping tube 26 and the index finger is disposed generally below the actuation surface 60 of the trigger member 54 to support the safety tube assembly 16. The operator will then depress the actuation surface 60 of the trigger member 54, and thereby automatically and virtually instantaneously withdraw the needle 18 through the catheter tube 30 and self-sealing injection port 40, and retract the needle 18 into the telescoping tube 26 and safety tube assembly 16 to be locked in that retracted position as disposed in a suitable manner for handling biohazards and sharps. The operator may then secure the catheter assembly 12 to the patient in using adhesive tape (but without the conventional need for looping the IV line), inject medication directly through the self-sealing injection port 40, or remove the vent cap 24 to expose the coupling 46 to attach a standard IV line in any order that is preferred.

If heparin locking is dictated, the operator injects heparin directly into the catheter assembly 12 via the self-sealing injection port 40, thereby flushing blood from the catheter assembly 12 and eliminating the possibility of blood clotting within the catheter assembly 12. Blood can also be flushed by injecting physiological saline or other medications, since the positive pressure of the injection will exceed any pressure exerted upstream along a connected IV line, and will close the check valve 38 to prevent backfeeding along the IV line.

Absent internal hydraulic pressure from an injection via the self-sealing injection port 40, the hydraulic pressure from the corresponding IV line will open the check valve 38 and allow liquid to flow into the catheter assembly 12 and be administered to the patient. Liquid from the IV line will also flush latent blood from the catheter assembly 12.

Because the vent cap assembly 24 and coupling 46 for the IV line are oriented in the same direction as the catheter tube 30 (that is, upwardly), it is unnecessary for the operator to loop the IV line before taping it to the patient, thus reducing the risk of the line getting hooked or caught on a projecting object as the patient is transported, kinking and requiring recatheterization with a new IV line, or snagging the operator's hand or instrument while other care is being provided.

A blood sample can be drawn or additional medications administered via the "shortest route possible" through the self-sealing injection port 40 without disengaging the IV line or recatheterizing the patient, since the "closed hub" catheter assembly 12 and check valve 38 permit both operations to be performed while the IV line is intact (although some operations may momentarily obstruct flow through the IV line while the check valve 3 8 is closed to maintain pressure within the catheter assembly 12.

After the patient is stabilized and being transported, the catheter assembly 12 and check valve 38 will continue to function. For example, if the IV line is accidentally lower to a point where siphoning would occur (or simply where IV flow would be interrupted), the check valve 38 will prevent blood from backing up and clotting within the IV line, saving the patient and operator the need to start a replacement IV. If the IV line is cut or becomes separated from the catheter assembly, there will be no blood loss or contamination since the check valve 38 and self-sealing injection port 40 will prevent blood from escaping the catheter assembly 12. If the operator needs to switch IV lines, they can do so quickly, safely, and without blood exposure since the check valve 38 permits the IV line to be removed and replaced at the coupling 46 without blood back-flow. One can also "piggy-back" more than one IV drip without the need for additional IV sites. Because the patient was catheterized and the initial IV started under sterile conditions due to the "closed hub" configuration of the catheter assembly 12, it may be unnecessary to recatheterize the patient at the hospital or health care facility when starting a replacement or additional IV.

It is understood that various changes, adaptations, and modifications may be made to the catheter system 10 and method of use described herein by those skilled in the art without departing from the spirit and scope of the appended claims.

I claim:

1. A catheter assembly for percutaneously introducing a liquid into a bloodstream of a patient from a conduit, said catheter assembly comprising:

a catheter housing defining an interior region, a first port, and a second port, the conduit being operatively connected to said first port in fluid communication therewith such that the liquid may flow from the conduit through said first port into said interior region of said catheter housing;

a catheter tube operatively connected to and extending from said catheter housing for percutaneous insertion into the bloodstream of the patient, said catheter tube defining a lumen fluidly communicating with said interior region of said catheter housing and a distal end received within the bloodstream of the patient such that the fluid may flow from the interior of the catheter housing into the bloodstream of the patient;

a check valve operatively connected to said catheter housing and fluidly communicating with said first port, said check valve preventing blood or the liquid within said interior of said catheter housing from flowing out through said first port; and a self-sealing injection site connected to said catheter housing in sealing relation to said second port, such that said catheter housing, said check valve, and said self-sealing injection site form a closed hub configuration external to the patient and to which the conduit is attached to introduce the liquid into the bloodstream of the patient.

2. The catheter assembly of claim 1 wherein the catheter assembly is an over-the-needle type in which a needle is initially received within the catheter tube, said needle having a distal end and a proximal end, a portion of the catheter tube and said distal end of said needle being inserted into a vessel of the patient, said needle being withdrawn from within the catheter tube leaving said portion of the catheter tube within said vessel in fluid communication within the bloodstream of the patient, said needle extending through the self-sealing injection site, the catheter assembly comprising:

a safety tube assembly, at least a portion of said safety tube assembly being retractable relative to the catheter housing, the proximal end of the needle being operatively connected to said safety tube assembly such that when said portion of said safety tube assembly is retracted the distal end of the needle is completely withdrawn through the self-sealing injection site and received within said safety tube assembly.

3. The catheter assembly of claim 2 for use by a user, said catheter assembly further comprising:

a latching mechanism for engaging and maintaining the portion of the safety tube which is retractable against rearward movement relative to the catheter housing, said latching mechanism including a trigger member; and a biasing mechanism for urging the portion of the safety tube which is retractable rearwardly relative to the catheter housing, such that when the user selectively actuates said trigger member said latching mechanism releases the portion of the safety tube assembly such that it retracts and withdraws the distal end of the needle completely into the safety tube assembly.

4. The catheter assembly of claim 2 wherein the safety tube may be removed from the catheter housing and disposed when the needle is completely withdrawn into the safety tube.

5. The catheter assembly of claim 2 wherein the safety tube includes a telescoping tube having a first segment and a second segment, said second segment being at least partially received within and sliding relative to said first segment, said first segment and said second segment together defining an interior region having a length greater than that of the needle when said second segment is fully retracted relative to said first segment.

6. The catheter assembly of claim 5 wherein the safety tube assembly further comprises:

a locking mechanism, said locking mechanism retaining the second segment in the retracted position relative to the first segment after the second segment has been retracted with the needle received within the interior region and the safety tube assembly removed from the catheter housing.

7. The catheter assembly of claim 1 wherein the catheter housing defines a body section having a longitudinal axis, a distal end, and a side, the catheter tube extending forwardly from said distal end generally parallel with said longitudinal axis, the first port extending forwardly from said side of said body section such that the first port and the conduit extend from the body section in generally the same direction as the catheter tube extends from said body section.

8. The catheter assembly of claim 7 wherein the first port and the body section define a generally U-shape, the first port having a first leg connected to and extending from the side of the body section generally perpendicular therewith, and a second leg connected to and end extending from said first leg generally perpendicular therewith, such that said second leg is generally parallel with the body section, said first leg and said second leg fluidly communicating with the body section.

9. The catheter assembly of claim 7 wherein the first port and the body section define a generally Y-shape, the first port extending from the side of the body section at a generally acute angle relative to the longitudinal axis, the first port fluidly communicating with the body section.

10. The catheter assembly of claim 9 wherein the generally acute angle is between 30° and 60°.

11. The catheter assembly of claim 9 wherein the generally acute angle is approximately 45°.

12. The catheter assembly of claim 1 wherein the catheter housing includes a body section having a side, and the first port includes a first leg extending from said side of said body section, the check valve being at least partially received within said first leg and moving between an open position and a closed position.

13. The catheter assembly of claim 12 wherein the check valve moves from the open position to the closed position in response to contact with the blood or the liquid within the body section of the catheter housing as the blood or the liquid traverses into the first leg of the first port.

14. The catheter assembly of claim 1 wherein the catheter housing includes a body section having a side, and the first port extends from said side of said body section and defines an end opening, and wherein the first port initially includes a vent cap assembly operatively connected to and disposed in covering relation to said end opening, said vent cap assembly being selectively removable from the first port such that the conduit may be connected to the first port.

15. The catheter assembly of claim 14 wherein the vent cap assembly defines an aperture having a filter element which permits the flow of gases therethrough.

16. The catheter assembly of claim 14 wherein the interior of the housing assembly and the end opening of the first port are initially sterile, and wherein the vent cap assembly maintains the sterility of the end opening until the vent cap assembly is selectively removed from the first port.

17. The catheter assembly of claim 1 for use by a user having a hand wherein the catheter housing defines a body section having a longitudinal axis, a side, a distal end, and an interior, the catheter tube extending forwardly from said distal end generally parallel with said longitudinal axis, the first port extending from said side of said body section, the catheter assembly including a needle at least partially received within the catheter tube and said interior region of said body section, said needle including a bore extending therethrough and an aperture fluidly communicating with said bore, at least a portion of said needle and the catheter tube being inserted into a vessel of the patient, the catheter housing further comprising:

a gripping region which may be gripped by the hand of the user for applying force to and advancing the catheter tube into the vessel of the patient, said gripping region being defined by at least a portion of either the body section or the first port or both; and a flash chamber region, said flash chamber region being defined by the body section and surrounding at least a portion of the interior region, said flash chamber region being sufficiently transparent to permit the user to visually observe the blood from the patient flowing through the aperture in the needle into the interior region of the body section, said flash chamber region being disposed between said gripping region and the catheter tube such that said flash chamber is disposed in front of the hand of the user.

18. The catheter assembly of claim 17 wherein the catheter tube is connected to and extends from the body section at a junction, and wherein the aperture in the needle is disposed generally proximate to said junction between the body section and the catheter tube.

19. The catheter assembly of claim 18 wherein the catheter tube has a proximal end and the aperture in the needle is disposed immediately behind and adjacent to said proximal end of the catheter tube.

20. The catheter assembly of claim 19 wherein the needle has a length extending between a distal end and a proximal end, and a side wall, the aperture extending through said side wall at a position disposed between said distal end and said proximal end.

21. The catheter assembly of claim 1 wherein the catheter assembly is an over-the-needle type in which a needle is initially received within the catheter tube, said needle having a distal end and a proximal end, a portion of the catheter tube and said distal end of said needle being inserted into a vessel of the patient, the catheter housing including a body section having a longitudinal axis, the catheter assembly comprising:

a safety tube assembly, the needle being selectively retracted through the self-sealing injection site and received within said safety tube assembly, said safety tube assembly being disposed generally behind the catheter housing opposing the catheter tube; and a grip member, said grip member being connected to and extending forwardly from said safety tube assembly at least partially surrounding the body section of the catheter housing, such that the hand of the user may grip said grip member and apply force to the safety tube assembly and in turn to the catheter housing in order to advance the catheter tube into the vessel of the patient.

22. The catheter assembly of claim 21 wherein the body section is a generally cylindrical tube, and wherein the grip member defines a partial cylinder disposed in circumscribing relation to at least a portion of the body section.

23. The catheter assembly of claim 22 wherein the body section has a top and a bottom, and the grip member is disposed is in circumscribing relation to at least said bottom of the body section.

24. The catheter assembly of claim 21 wherein the body section has a length measured from the proximal end thereof and the grip member extends forwardly more than half said length of the body section.

25. The catheter assembly of claim 1 to be used by a user having a hand with a fingertip, wherein the catheter assembly is an over-the-needle type in which a needle is initially received within the catheter tube, said needle having a distal end and a proximal end, a portion of the catheter tube and said distal end of said needle being inserted into a vessel of the patient, the catheter housing including a body section having a longitudinal axis and an outer surface, the catheter assembly comprising:

a push flange, said push flange disposed on the body section of the catheter housing and extending radially outward relative to the outer surface of the body section such that the user may engage the push flange with the fingertip to apply force to and advance the catheter tube into the vessel of the patient.

26. The catheter assembly of claim 25 wherein the push flange has a generally irregular shape such that the push flange extends a distance further from the longitudinal axis in a first region than in a second region.

27. The catheter assembly of claim 26 wherein the push flange is rotatably mounted on the body section such that the first section may be rotated to a plurality of different positions around the body section of the catheter housing.

28. The catheter assembly of claim 25 wherein the push flange has a generally irregular shape such that the push flange extends a distance further from the longitudinal axis in a first pair of regions than in a second pair of regions, said first pair of regions being disposed generally diametrically opposed to one another relative to the body section of the catheter housing.

29. A method for percutaneously introducing a liquid into a bloodstream of a patient from a reservoir through a conduit using an over-the-needle type catheter, said over-the-needle type catheter including a needle having a distal tip which is inserted into a vessel of said patient, said method comprising the steps of:

providing a catheter assembly having a catheter housing defining an interior region, a first port, and a second port, a catheter tube operatively connected to and extending from said catheter housing, said catheter tube defining a lumen fluidly communicating with said interior region of said catheter housing and a distal end, said catheter tube receiving at least a portion of the needle therein, a check valve operatively connected to said catheter housing and fluidly communicating with said first port, and a self-sealing injection site connected to said catheter housing in sealing relation to said second port, said catheter housing, said check valve, and said self-sealing injection site forming a closed hub configuration external to the patient;

inserting a portion of the needle and said catheter tube into the vessel of the patient in fluid communication with the bloodstream;

retracting the needle from the vessel of the patient and through said catheter housing and said self-sealing injection site; and connecting the conduit to said first port such that the fluid may flow from the reservoir through the conduit into said interior region of said catheter housing and into the bloodstream of the patient, said check valve preventing the blood or the liquid within said interior region of said catheter housing from flowing from said interior region of said catheter housing out through said first port.

30. The method of claim 29 wherein the needle and the catheter tube are gripped and advanced into the vessel of the patient by a user having a hand, the catheter housing further defines a gripping region and a flash chamber, said flash chamber permitting said user to visually observe the blood from the patient entering the interior region from the needle as the distal tip of the needle is advanced into the vessel, the flash chamber being disposed between the gripping region and the catheter tube, the step of inserting the portion of the needle and the catheter tube into the vessel of the patient in fluid communication with the bloodstream further comprising the step of:

observing the initial flow of blood into the interior region of the catheter housing from the needle at a position within the flash chamber disposed between the catheter tube and the hand of the user advancing the needle and the catheter tube.

31. The method of claim 29 further comprising the step of:

administering an agent into the blood stream of the patient by injecting said agent through the self-sealing injection site using a syringe.

32. The method of claim 31 wherein the step of administering the agent into the blood stream of the patient through the self-sealing injection site using the syringe is accomplished without disconnecting the conduit from the first port, the check valve preventing the agent from entering the conduit.

33. The method of claim 29 further comprising the step of:

administering an agent into the blood stream of the patient connecting a second conduit to the second port.

34. The method of claim 33 further comprising the step of:

administering a second agent into the blood stream of the patient by injecting said second agent through the self-sealing injection site using a syringe while the second conduit remains connected to the second port.

35. The method of claim 29 further comprising the step of:

flushing the interior region of the catheter housing by injecting a flushing liquid through the self-sealing injection site or the first port using a syringe.

36. The method of claim 35 wherein the flushing liquid is injected through the self-sealing injection site and the check valve prevents the flushing liquid from entering the conduit.

37. The method of claim 29 further comprising the step of:

withdrawing a blood sample from the bloodstream of the patient through the self-sealing injection site while the conduit remains connected to the first port, whereby the check valve prevents the blood sample from entering the conduit.

38. The method of claim 29 further comprising the step of:

removing the conduit from the first port, the check valve preventing the blood or the liquid within the interior region from flowing through the first port; and connecting a second conduit to the first port.

39. The method of claim 29 wherein the first port includes an end opening which is initially sterile and a vent cap assembly disposed in covering relation to said end opening, said vent cap assembly maintaining the sterility of the end opening, the method comprising the step of:

removing the vent cap assembly from the end opening of the first port prior to connecting the conduit to the first port, the check valve preventing the blood within the interior region of the catheter housing from flowing from the interior region of the catheter housing out through said first port when the vant cap assembly is removed.

* * * * *